(12) United States Patent
Quintanilha

(10) Patent No.: US 9,261,772 B2
(45) Date of Patent: Feb. 16, 2016

(54) LITHOGRAPHIC APPARATUS, SUBSTRATE AND DEVICE MANUFACTURING METHOD

(71) Applicant: ASML Netherlands B.V., Veldhoven (NL)

(72) Inventor: Richard Quintanilha, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 227 days.

(21) Appl. No.: 13/853,407

(22) Filed: Mar. 29, 2013

(65) Prior Publication Data

US 2013/0271740 A1 Oct. 17, 2013

Related U.S. Application Data

(60) Provisional application No. 61/624,590, filed on Apr. 16, 2012.

(51) Int. Cl.
| | |
|---|---|
| G03B 27/54 | (2006.01) |
| G03F 1/00 | (2012.01) |
| G01N 21/93 | (2006.01) |
| G03F 7/20 | (2006.01) |
| G01N 21/956 | (2006.01) |

(52) U.S. Cl.
CPC ............... *G03F 1/144* (2013.01); *G01N 21/93* (2013.01); *G01N 21/956* (2013.01); *G03F 7/70641* (2013.01); *G03F 7/70683* (2013.01)

(58) Field of Classification Search
CPC ........................ G03F 7/70641; G03F 9/9089

USPC ........ 355/52, 53, 55, 67; 356/237.2, 620–624
See application file for complete search history.

(56) References Cited

U.S. PATENT DOCUMENTS

| | | | |
|---|---|---|---|
| 2008/0002213 A1* | 1/2008 | Weiss ........................... 356/620 |
| 2008/0298222 A1* | 12/2008 | Hirose et al. ............... 369/275.4 |
| 2011/0027704 A1 | 2/2011 | Cramer et al. | |
| 2011/0043791 A1 | 2/2011 | Smilde et al. | |
| 2012/0113404 A1 | 5/2012 | Hsu et al. | |

FOREIGN PATENT DOCUMENTS

| | | |
|---|---|---|
| EP | 0 701 174 A1 | 3/1996 |
| JP | 10-050528 A | 2/1998 |
| WO | WO 2009/078708 A1 | 6/2009 |
| WO | WO 2009/1550089 * | 6/2009 |
| WO | WO 2009/106279 A1 | 9/2009 |

OTHER PUBLICATIONS

English-Language Abstract for Japanese Patent Publication No. 10-050528 A, published Feb. 20, 1998; 1 page.

* cited by examiner

*Primary Examiner* — Hung Henry Nguyen
(74) *Attorney, Agent, or Firm* — Sterne, Kessler, Goldstein & Fox, P.L.L.C.

(57) ABSTRACT

A method uses a lithographic apparatus to form an inspection target structure upon a substrate. The method comprises forming the periphery of the inspection target structure so as to provide a progressive optical contrast transition between the inspection target structure and its surrounding environment. This may be achieved by providing a progressive change in the optical index at the periphery of the target structure.

29 Claims, 8 Drawing Sheets

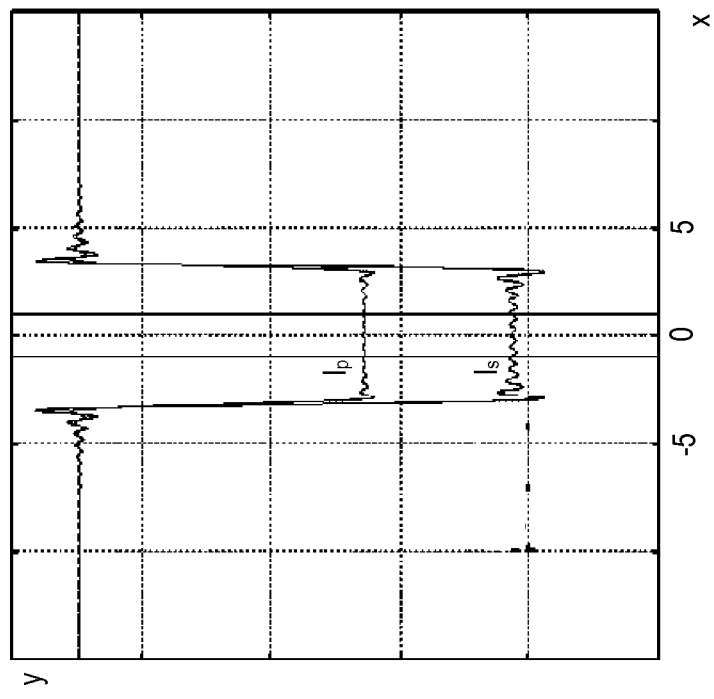
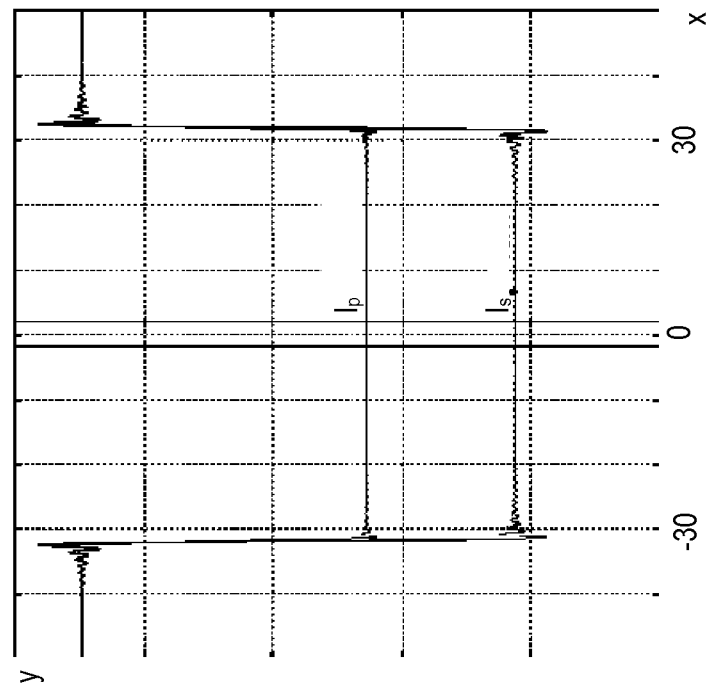

LITHOGRAPHIC APPARATUS, SUBSTRATE AND DEVICE MANUFACTURING METHOD

BACKGROUND

1. Field of the Invention

The present invention relates to methods of inspection usable, for example, in the manufacture of devices by lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Diffraction-based overlay using dark-field detection of the diffraction orders enables overlay measurements on smaller targets. These targets can be smaller than the illumination spot and may be surrounded by product structures on a wafer. Multiple targets can be measured in one image.

SUMMARY

It is desirable to be able to provide better quality and/or smaller inspection targets.

According to an aspect of the present invention, there is provided a method of using a lithographic apparatus to form an inspection target structure upon a substrate, the method comprising forming the periphery of the inspection target structure so as to provide a progressive optical contrast transition between the inspection target structure and its surrounding environment.

According to a second aspect of the present invention, there is provided a lithographic apparatus comprising: an illumination system configured to condition a radiation beam, a support constructed to support a patterning device, the patterning device being capable of imparting the radiation beam with a pattern in its cross-section to form a patterned radiation beam, a substrate table constructed to hold the substrate, and a projection system configured to project the patterned radiation beam onto a target portion of the substrate, wherein the lithographic apparatus is configured to form upon the substrate an inspection target structure, a periphery of the inspection target structure being formed so as to provide a progressive optical contrast transition between the inspection target structure and its surrounding environment.

According to a third aspect of the present invention, there is provided a substrate having a target structure formed thereon by a lithographic process, the periphery of the target structure being formed so as to provide a progressive optical contrast transition between the inspection target structure and its surrounding environment.

According to a fourth aspect of the present invention, there is provided a computer program product comprising program instructions operable to cause a suitable lithographic apparatus to perform the method of the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 6a and 6b show intensity plots for a relatively large target and a smaller target respectively.

Figure 1:
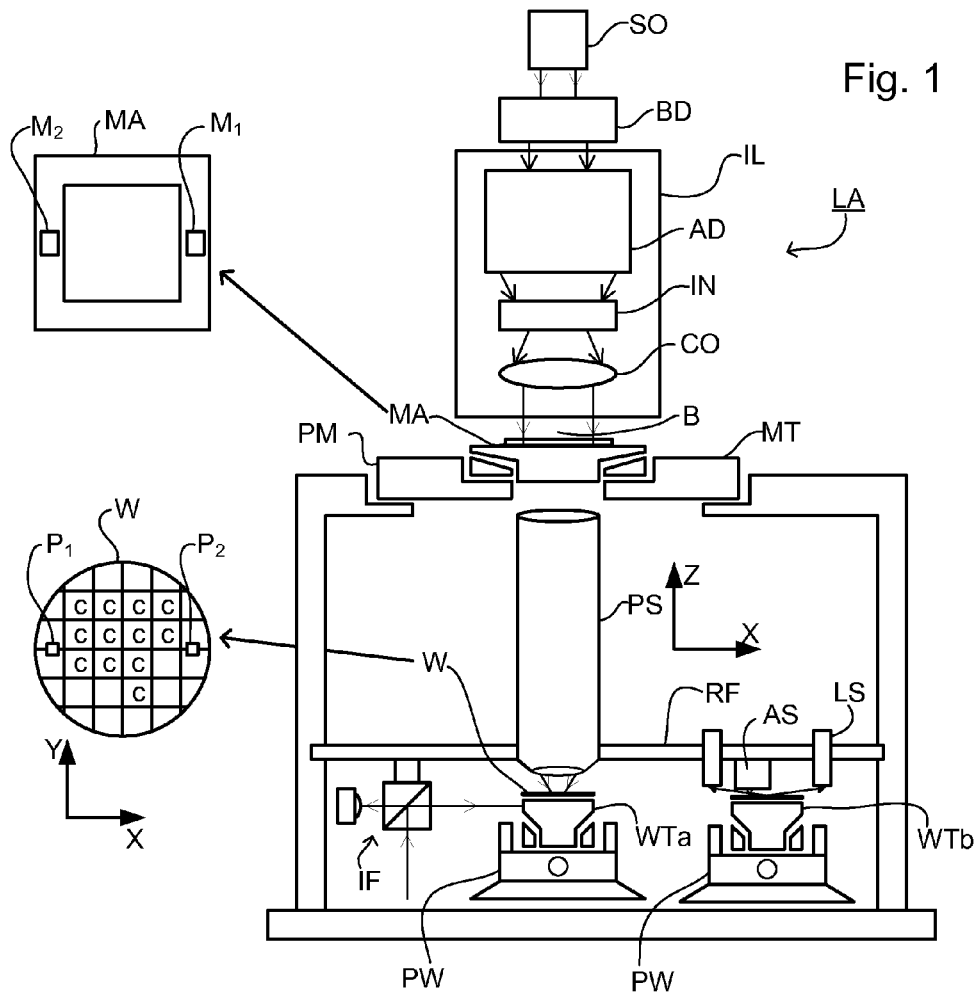
FIG. 1 depicts a lithographic apparatus according to an embodiment of the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention.

The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions.

The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
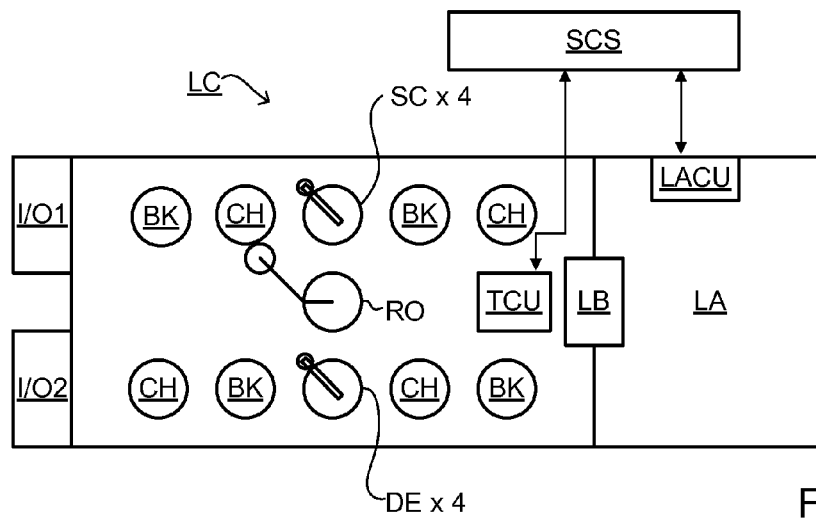
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Examples of dark field metrology can be found in international patent applications WO 2009/078708 and WO 2009/106279, which documents are hereby incorporated by reference in their entirety. Further developments of the technique have been described in patent publications U.S. Publ. 20110027704A and U.S. Publ. 20110043791A and in U.S. patent application 61/412,980, filed 10 Nov. 2010, not published at the present priority date. The contents of all these applications are also incorporated herein by reference.

Figure 3A:
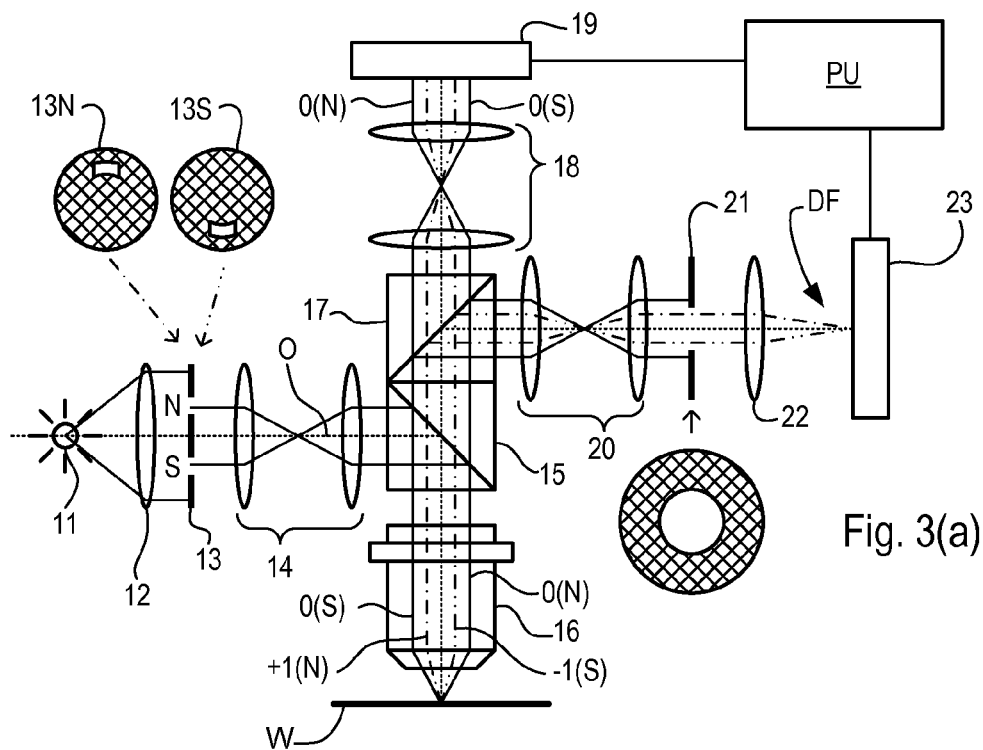
FIG. 3(a) shows schematic diagram of a dark field scatterometer for use in measuring targets according to embodiments of the invention using a first pair of illumination apertures and 3(b) shows detail of diffraction spectrum of a target grating for a given direction of illumination.

A dark field metrology apparatus suitable for use in embodiments of the invention is shown in FIG. 3(a). A target grating T and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

Figure 3B:
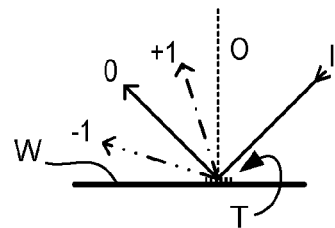

As shown in FIG. 3(b), target grating T is placed with substrate W normal to the optical axis O of objective lens 16. A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g., a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target on the substrate W on sensor 23 (e.g., a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial sight modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 4, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 5, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 4:
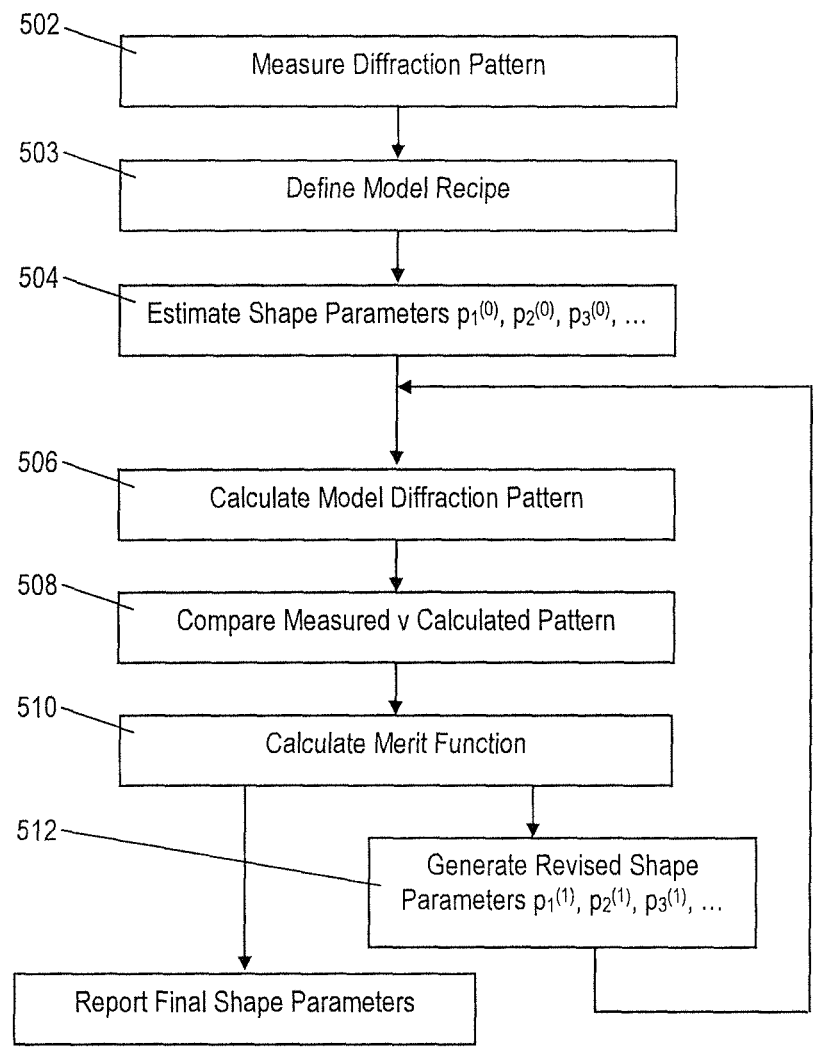
FIG. 4 depicts a first example process for reconstruction of a structure from scatterometer measurements.

Referring to FIG. 4 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters pi (p1, p2, p3 and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, ways will be introduced in which parameters can be permitted to vary without being fully independent floating parameters. For the purposes of describing FIG. 4, only the variable parameters are considered as parameters pi.

In step 504: A model target shape is estimated by setting initial values pi(0) for the floating parameters (i.e., p1(0), p2(0), p3(0) and so on). Each floating parameter will be generated within certain predetermined ranges, as defined in the recipe.

In step 506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508, 510: The measured diffraction pattern and the model diffraction pattern are then compared and their similarities and differences are used to calculate a "merit function" for the model target shape.

In step 512: Assuming that the merit function indicates that the model needs to be improved before it represents accurately the actual target shape, new parameters p1(1), p2(1), p3(1), etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e., the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502 For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 4 onward, the term 'diffraction pattern' will be used, on the assumption that the scatterometer of FIG. 4 is used. The skilled person can readily adapt the teaching to different types of scatterometer, or even other types of measurement instrument.

Figure 5:
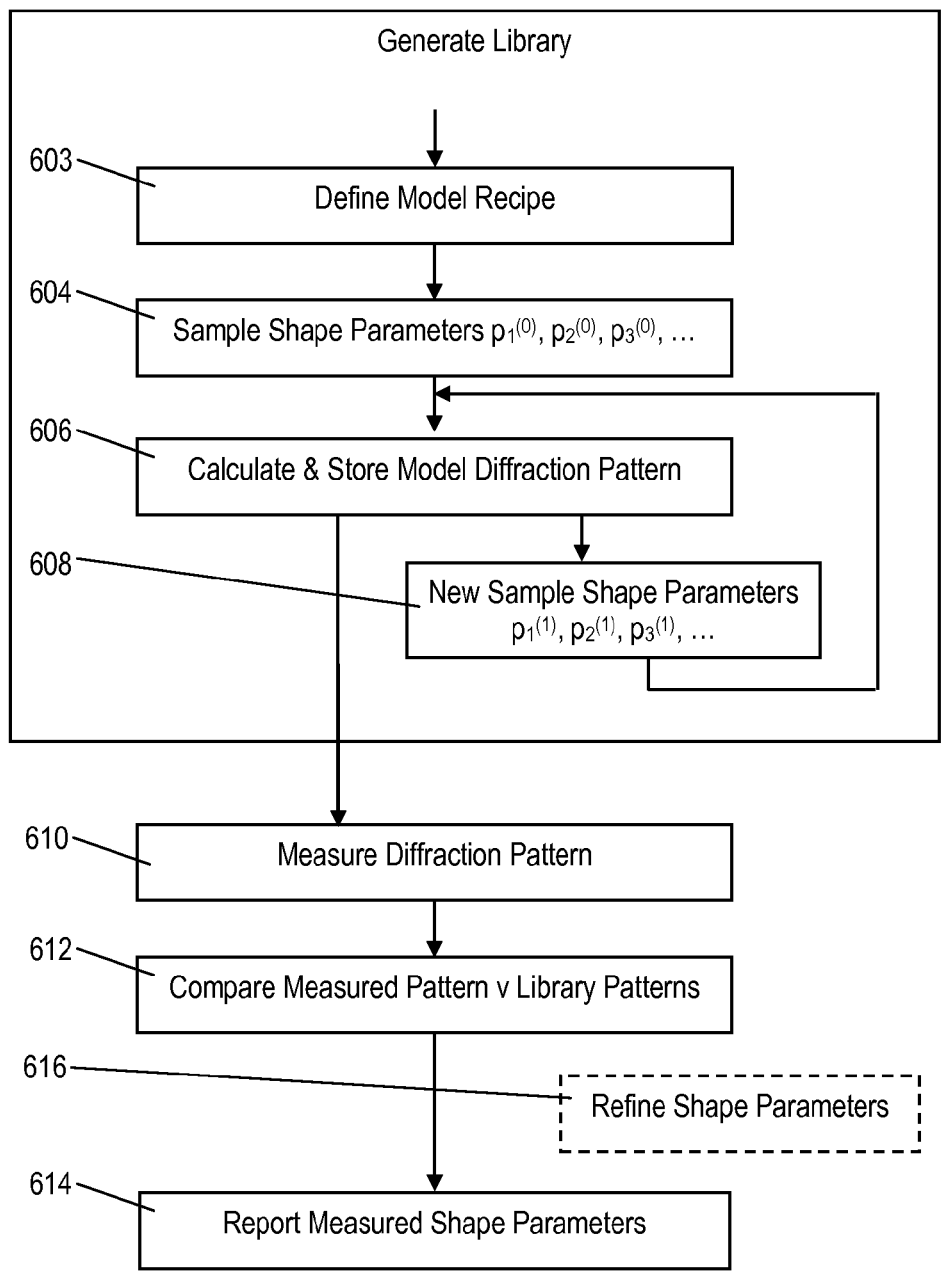
FIG. 5 depicts a second example process for reconstruction of a structure from scatterometer measurements.

FIG. 5 illustrates an alternative example process in which plurality of model diffraction patterns for different estimated target shapes (candidate structures) are calculated in advance and stored in a library for comparison with a real measurement. The underlying principles and terminology are the same as for the process of FIG. 4. The steps of the FIG. 5 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters pi (p1, p2, p3 and so on). Considerations are similar to those in step 503 of the iterative process.

In step 604: A first set of parameters p1(0), p2(0), p3(0), etc. is generated, for example by generating random values of all the parameters, each within its expected range of values.

In step 606: A model diffraction pattern is calculated and stored in a library, representing the diffraction pattern expected from a target shape represented by the parameters.

In step 608: A new set of shape parameters p1(1), p2(1), p3(1), etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 4, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e., the calculation of the estimated model diffraction pattern using a rigorous optical diffraction theory from the estimated target shape.

It is desirable to put such metrology targets on the actual product (for example, in scribe lanes) so as to be able to perform measurement in-die. As design rules shrink, metrology targets are also required to be smaller to fit into the smaller scribe lanes (or wherever they are placed). In particular, performing optical critical-dimension (OCD) measurements on metrology targets, such as gratings, that are smaller than the illumination spot (field of view) presents a real challenge. One way of measuring metrology target properties smaller than the illumination spot is to use an angle resolved imaging microscope (ARIM). Another way uses brightfield or darkfield microscopy to measure μOCD metrology targets.

One of the main limitations in reducing the target size is that the edge diffraction effect becomes increasingly significant and therefore difficult to take into account in the measurement. FIGS. 6a and 6b illustrate this. They show intensity profiles obtained from inspection of two finite line gratings using normal incident illumination (traces for both s-polarized $I_s$ and p-polarized $I_p$ illumination are shown). In each case intensity is on the y axis and position across the grating (in μm) is on the x axis. FIG. 6a shows such an intensity profile for a 32 μm×32 μm grating while FIG. 6b shows the intensity profile for a 6.5 μm×6.5 μm grating. These two profiles show the diffraction edge effect. In FIG. 6a the edge effect is much less significant in relation to the whole plot, and can be more easily discounted by considering the central region (region of interest) around position 0. However, in FIG. 6b the edge effect causes oscillations across the whole profile, making accurate measurement much more difficult.

The edge diffraction effect is caused mainly by optical contrast between the grating and surrounding atmosphere. It is therefore proposed to modify the edge of the target in as to reduce or attenuate the optical contrast. This will improve the quality of the metrology target, offering the possibility to make it smaller.

Figure 7:
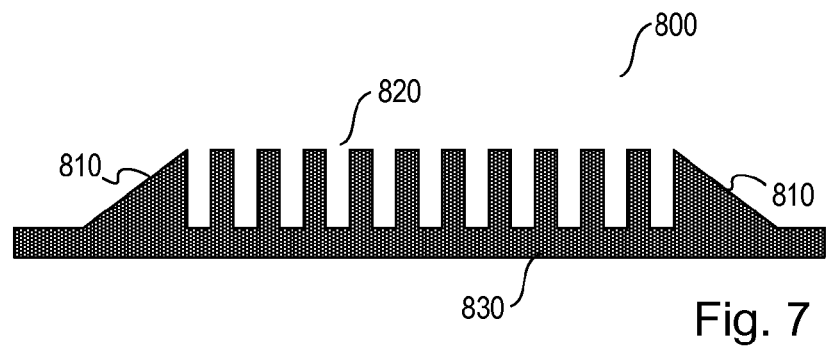
FIG. 7 shows a metrology target according to a first embodiment of the invention.

The target edge modification may comprise making the optical contrast smoother (thereby providing an optical gradient) at the periphery of the target. FIG. 7 illustrates one embodiment of a target 800 comprising a grating 820 on a substrate 830. The target 800 has an edge modification 810 that provides a smooth optical transition between grating 820 and the surrounding atmosphere. As can be seen the edge modification 810 comprises increasing the edge length from zero (a vertical edge) to non-zero (a sloped edge). This non-zero edge length may be in the order of magnitude of ten wavelengths of the incident light, or in the range of 1 to 100 wavelengths for example. Over this edge length the height of the resist which forms the target 800 may rise substantially uniformly (or in uniform steps) from the substrate to the grating 820 height.

Figure 8:
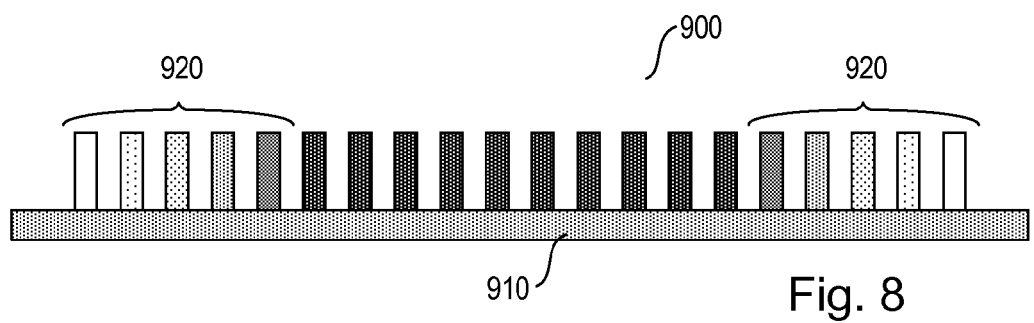
FIG. 8 shows a metrology target according to a second embodiment of the invention.

FIG. 8 illustrates a further embodiment of a target 900 on substrate 910, having a smoothed optical contrast at the target's edge. In this embodiment the optical indices of lines at the target periphery are varied. In the example shown, the outermost five lines 920 have progressively different optical indices towards the target edge in order to smooth out the transition from the atmosphere to that of the grating. This is shown here by the progressive change in shading of the outermost five lines 920. The actual number of lines over which the optical contrast is smoothed may vary, and may be any number up to 10, up to 20, up to 50 or up to 100, for example. The optical gradient may be obtained, for instance, by using effective medium theory. There are a number of different ways that the optical index may be smoothed over the outermost lines of the target. By way of example, FIGS. 9 and 10 illustrate two such examples.

Figure 9:
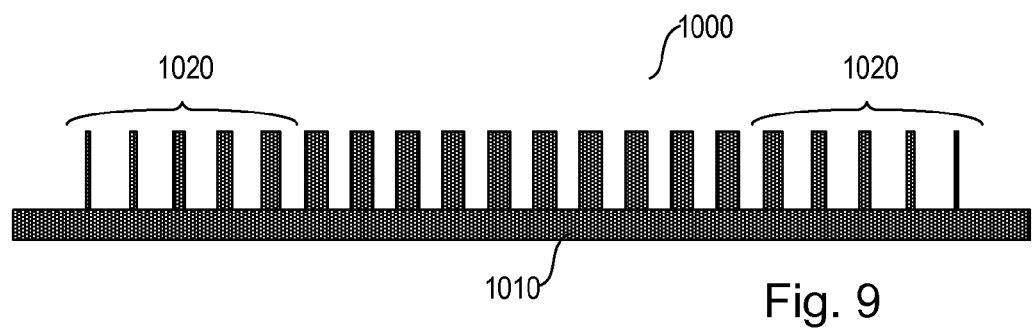
FIG. 9 shows a first variation on the metrology target of FIG. 8.
Figure 10:
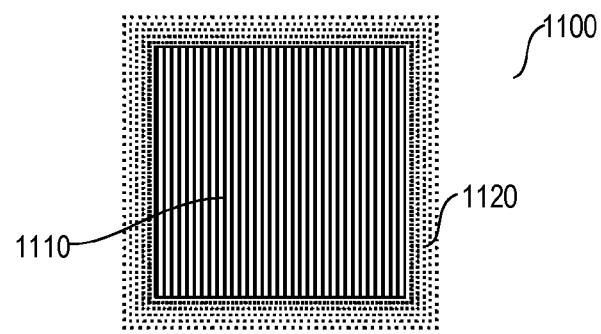
FIG. 10 shows a second variation on the metrology target of FIG. 8.

FIG. 9 shows a target 1000 on a substrate 1010, wherein the outermost lines 1020 (five shown in this example) progressively become thinner towards the target edge. FIG. 10 shows a target 1100 shown from above, comprising grating 1110 and edge modification 1120. Edge modification 1120 comprises the outermost lines being broken or dotted, each line having a different dotted pitch, thereby resulting in an effective optical index which changes progressively from grating 1110 and the surrounding atmosphere.

It is notable that the concepts described herein can be obtained using methods that are similar to Optical Proximity Correction (OPC) methods used in lithography to improve pattern printing. OPC is well known and will not be discussed in any detail here. Accordingly, the mask used to print the target onto the substrate is modified to obtain the desired target edge modification using techniques that are similar to OPC techniques, where the pattern on the mask is altered to compensate for image errors due to diffraction or process effects.

It is preferable that any OPC-like objects added to the mask in order to obtain the desired edge modifications, comprise those which are found within current OPC rules so as to keep the mask cost as low as possible. For instance while the dotted lines of FIG. 10 are perfectly feasible, they are very expensive. This is because dotted lines that have the same node size as linewidth are never put on the same mask under current rules. To remain within current rules, the dots should be two to three times longer than their width. Therefore, the FIG. 9 example is preferred as this can be more easily printed using current OPC design rules.

The concepts described herein result in an improvement of the optical signature, due to the reduction of the diffraction effect of the edge of the target onto the center of the target. This reduction is a consequence of the reduction or elimination of the oscillation propagation of the electromagnetic field induced by the finite dimension of the target.

Figure 11A:
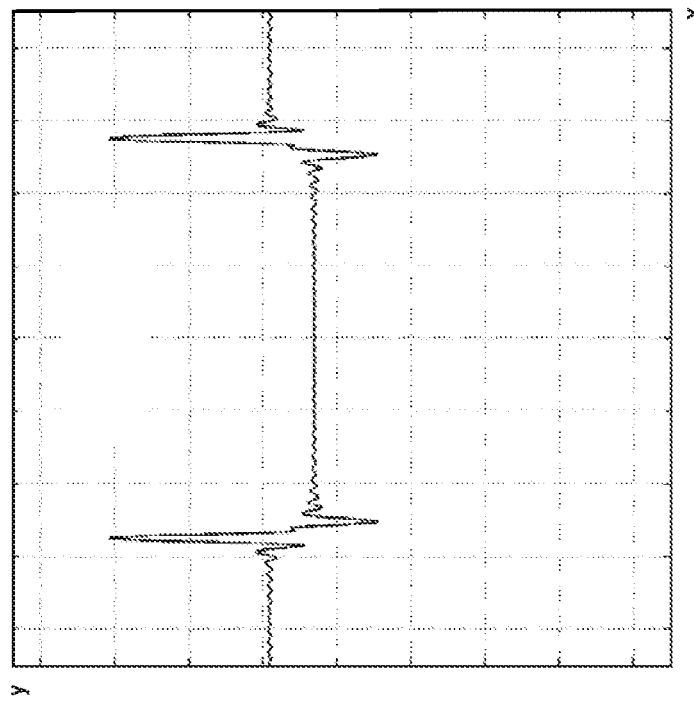
FIGS. 11a and 11b show intensity plots for an unmodified target and for one modified according to the first embodiment of the invention.
Figure 11B:
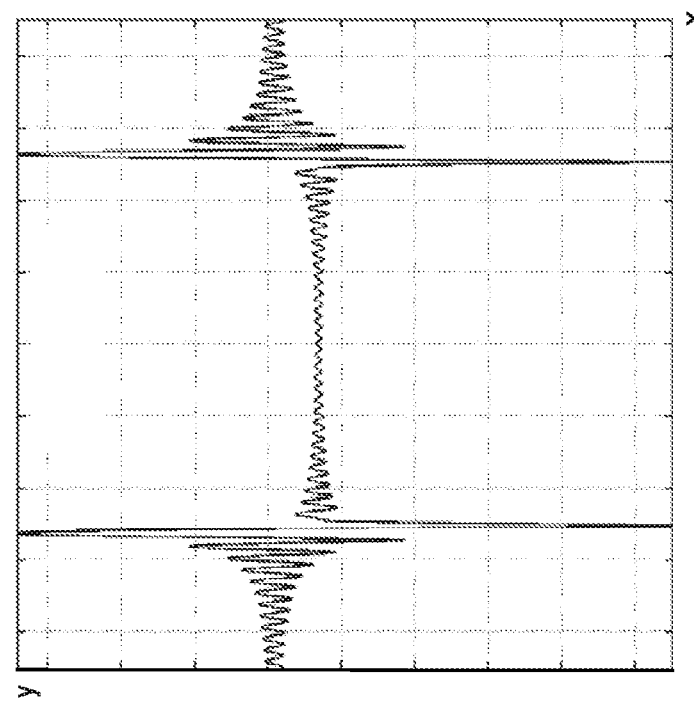

FIGS. 11a and 11b illustrate this reduction of the diffraction effect for the embodiment illustrated in FIG. 7. FIG. 11a shows an intensity profile obtained from inspection of a small (less than 12 μm), finite line grating with no edge modification. FIG. 11b shows an intensity profile obtained from inspection a similar finite line grating, but with an edge modification similar to that illustrated in FIG. 7 (in this example the edge length is 10 times the incident radiation wavelength). In each case intensity is on the y axis and position across the grating is on the x axis. It can be seen that the edge effect oscillations are significantly reduced in FIG. 11b, compared to FIG. 11a, with very little oscillation around the center of the profile.

Figure 12A:
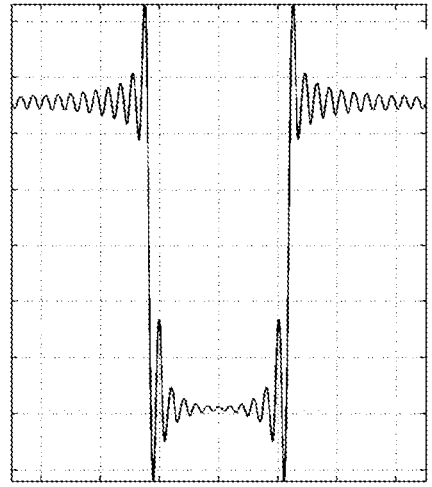
FIGS. 12a and 12b show intensity plots for an unmodified target and for one modified according to the second embodiment of the invention under first illumination conditions.
Figure 13A:
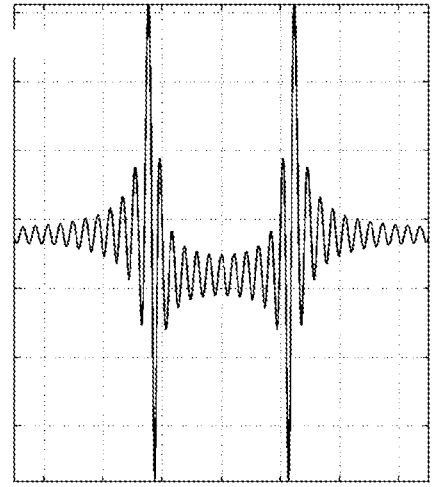
FIGS. 13a and 13b show intensity plots for an unmodified target and for one modified according to the second embodiment of the invention under second illumination conditions.
Figure 12B:
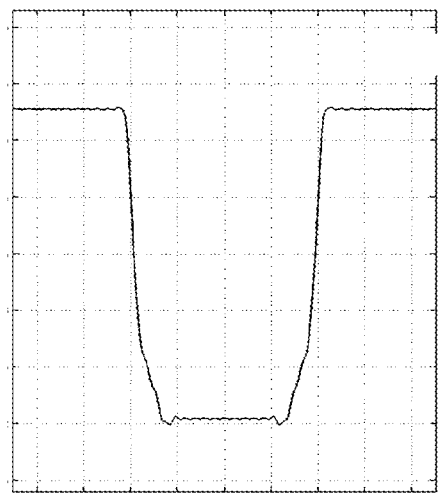
Figure 13B:
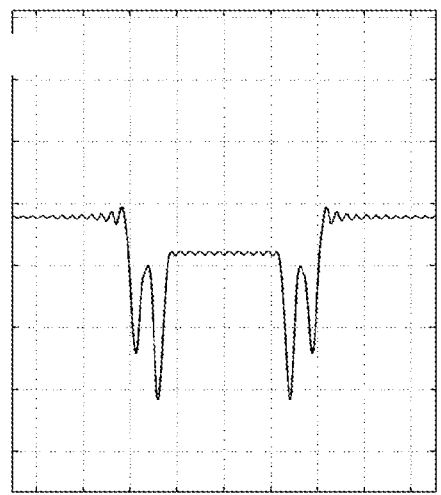

FIGS. 12a and 13a both show an intensity profile obtained from inspection of a small (less than 12 μm), finite line grating with no edge modification. In FIG. 12a, the incident illumination is p-polarized and in FIG. 13a, the incident illumination is s-polarized. FIGS. 12b and 13b show a similar target under corresponding illumination conditions to FIGS. 12a and 13a respectively, but with an edge modification similar to that illustrated in FIG. 8 (in this example the number of modified lines is 20). In both cases it can again be seen that the edge effect oscillations are significantly reduced compared to the unmodified target.

These Figures represent an ideal case with a single incident plane wave. In actuality, the edge diffraction will be smoothed out by the fact that the a real source has a spectrum width and that the angle of illumination is a cone of illumination.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below. In particular, it should be appreciated that many different target edge modifications can be implemented including many within the scope of the invention not described here. The target design may be ultimately chosen based upon its feasibility and/or cost with a particular optical lithography tool, and current materials and processes of the semiconductor industry.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
    illuminating a target structure using a spot size that is larger than the target structure, wherein the target structure includes a progressive optical contrast transition at peripheral edges of the target structure; and
    measuring a diffraction pattern of the target structure, wherein a diffraction effect at the peripheral edges of the target structure is substantially reduced by the progressive optical contrast transition.

2. The method of claim 1, wherein the progressive optical contrast transition provides a progressive change in the optical index at the peripheral edges of the target structure.

3. The method of claim 2, wherein the progressive optical contrast transition includes an outermost element along one or more of the target structure's peripheral edges, the height of the element decreasing towards the peripheral edge.

4. The method of claim 3, wherein the outermost element is wider than the other elements of which the target structure is comprised.

5. The method of claim 2, wherein:
    the progressive optical contrast transition includes peripheral elements along one or more of the target structure's peripheral edges; and
    along any one peripheral edge, the optical index of each peripheral element differs progressively toward the peripheral edge.

6. The method of claim 5, wherein the peripheral elements are lines wherein, along any one peripheral edge, the line width of each line decreases progressively toward the peripheral edge.

7. The method of claim 5, wherein:
    the peripheral elements are broken lines; and
    along any one peripheral edge, the ratio of line element to line break for each broken line decreases progressively toward the peripheral edge.

8. The method of claim 1, wherein the progressive optical contrast transition is formed by altering the patterning device using Optical Proximity Correction techniques.

9. The method of claim 1, wherein the target structure is smaller than about 12 μm along any edge of the target structure.

10. The method of claim 1, wherein the target structure is a repetitive structure usable by an inspection apparatus for measuring a parameter of the lithographic process.

11. The method of claim 1, further comprising:
    using an inspection apparatus to perform a measurement of an aspect of the target structure and to determine a parameter of a lithographic process from the measurement.

12. A substrate comprising:
    a target structure formed thereon by a lithographic process, the target structure including a progressive optical contrast transition at peripheral edges of the target structure, wherein the progressive optical contrast transition is configured to reduce a diffraction effect at the peripheral edges of the target structure when the target structure is illuminated with a spot size that is larger than the target structure.

13. The substrate of claim 12, wherein the progressive optical contrast transition provides a progressive change in the optical index at the peripheral edges of the target structure.

14. The substrate of claim 13, wherein the progressive optical contrast transition includes an outermost element along one or more of the target structure's peripheral edges, the height of the element decreasing towards the peripheral edge.

15. The substrate of claim 14, wherein the outermost element is wider than the other elements of which the target structure is comprised.

16. The substrate of claim 13, wherein:
the progressive optical contrast transition includes peripheral elements along one or more of the target structure's peripheral edges; and
along any one peripheral edge, the optical index of each peripheral element differs progressively toward the peripheral edge.

17. The substrate of claim 16, wherein:
the peripheral elements are lines; and
along any one peripheral edge, the line width of each line decreases progressively toward the peripheral edge.

18. The substrate of claim 16, wherein:
the peripheral elements are broken lines; and
along any one peripheral edge, the ratio of line element to line break for each broken line decreases progressively toward the peripheral edge.

19. The substrate of claim 12, wherein the target structure is smaller than 12 µm along any edge of the target structure.

20. The substrate of claim 12, wherein the target structure is a repetitive structure usable by an inspection apparatus for measuring a parameter of the lithographic process.

21. A non-transitory computer-readable storage device having instructions stored thereon, execution of which, by a computing device, causes the computing device to control an inspection apparatus to perform operations comprising:
illuminating a target structure using a spot size that is larger than the target structure, wherein the target structure includes a progressive optical contrast transition at peripheral edges of the target structure; and
measuring a diffraction pattern of the target structure, wherein a diffraction effect at the peripheral edges of the target structure is substantially reduced by the progressive optical contrast transition.

22. An inspection apparatus, comprising:
an optical system configured to direct a radiation beam onto a target structure patterned on a wafer, wherein the target structure includes a progressive optical contrast transition at peripheral edges of the target structure; and
one or more sensors configured to receive light from the target structure,
wherein a spot size of the radiation beam is larger than the target structure, and
wherein a diffraction effect at the peripheral edges of the target structure is substantially reduced by the progressive optical contrast transition.

23. The inspection apparatus of claim 22, wherein the progressive optical contrast transition includes a progressive change in the optical index at the peripheral edges of the target structure.

24. The inspection apparatus of claim 23, wherein the progressive optical contrast transition includes an outermost element along one or more of the target structure's peripheral edges, the height of the element decreasing towards the peripheral edge.

25. The inspection apparatus of claim 24, wherein the outermost element is made wider than the other elements of which the target structure is comprised.

26. The inspection apparatus of claim 23, wherein:
the progressive optical contrast transition includes peripheral elements along one or more of the target structure's peripheral edges; and
along any one peripheral edge, the optical index of each peripheral element differs progressively toward the peripheral edge.

27. The inspection apparatus of claim 26, wherein:
the peripheral elements are lines; and
along any one peripheral edge, the line width of each line decreases progressively toward the peripheral edge.

28. The inspection apparatus of claim 26, wherein:
the peripheral elements are broken lines; and
along any one peripheral edge, the ratio of line element to line break for each broken line decreases progressively toward the peripheral edge.

29. The inspection apparatus of claim 22, wherein the target structure is smaller than about 12 µm along any edge.

* * * * *